(12) United States Patent
Siu et al.

(10) Patent No.: US 11,039,765 B2
(45) Date of Patent: Jun. 22, 2021

(54) SMART PELLET FOR SAMPLE TESTING

(71) Applicant: International Business Machines Corporation, Armonk, NY (US)

(72) Inventors: Vince Siu, Thornhill (CA); Minhua Lu, Mohegan Lake, NY (US); Evan Colgan, Montvale, NJ (US); Russell Budd, North Salem, NY (US); John U. Knickerbocker, Monroe, NY (US)

(73) Assignee: International Business Machines Corporation, Armonk, NY (US)

( * ) Notice: Subject to any disclaimer, the term of this patent is extended or adjusted under 35 U.S.C. 154(b) by 479 days.

(21) Appl. No.: 15/715,558

(22) Filed: Sep. 26, 2017

(65) Prior Publication Data
US 2019/0090791 A1  Mar. 28, 2019

(51) Int. Cl.
| | |
|---|---|
| *A61B 5/145* | (2006.01) |
| *G01N 21/64* | (2006.01) |
| *G01N 33/543* | (2006.01) |
| *G01N 33/558* | (2006.01) |
| *G16H 10/40* | (2018.01) |
| *G01N 21/78* | (2006.01) |
| *G01N 21/84* | (2006.01) |

(52) U.S. Cl.
CPC ...... *A61B 5/14507* (2013.01); *A61B 5/14532* (2013.01); *G01N 21/6428* (2013.01); *G01N 21/78* (2013.01); *G01N 21/8483* (2013.01); *G01N 33/54366* (2013.01); *G01N 33/558* (2013.01); *G16H 10/40* (2018.01); *A61B 5/14539* (2013.01); *G01N 2201/0218* (2013.01)

(58) Field of Classification Search
CPC .... G16H 10/40; G01N 21/6428; G01N 21/78; G01N 21/8483; G01N 33/54366; G01N 33/558
USPC ...................................... 422/82.05
See application file for complete search history.

(56) References Cited

U.S. PATENT DOCUMENTS

| | | | |
|---|---|---|---|
| 3,443,903 | A | 5/1969 | Haack et al. |
| 4,116,066 | A | 9/1978 | Mehl et al. |
| (Continued) | | | |

FOREIGN PATENT DOCUMENTS

| | | |
|---|---|---|
| CN | 202776284 U | 3/2013 |
| WO | WO2009094761 A1 | 8/2009 |
| (Continued) | | |

OTHER PUBLICATIONS

Adhikari et al., "Carbon Nanomaterials Based Electrochemical Sensors/Biosensors for the Sensitive Detection of Pharmaceutical and Biological Compounds," Sensors Sep. 2015, 15, 22490-22508.

(Continued)

*Primary Examiner* — Benjamin R Whatley
*Assistant Examiner* — Jacqueline Brazin
(74) *Attorney, Agent, or Firm* — Kristofer Haggerty; Michael J. Chang, LLC (57) ABSTRACT

A submersible sensor device configured as a small pellet for testing biological and other liquid samples is provided. In one aspect, a sensing device includes: a housing; and one or more sensors contained within the housing, wherein the housing hermetically seals the sensors such that the sensing device is fully submersible in a liquid analyte. A method and system for analysis of a liquid sample using the present sensing device are also provided.

22 Claims, 9 Drawing Sheets

(56) References Cited

U.S. PATENT DOCUMENTS

| | | | |
|---|---|---|---|
| 5,310,526 A * | 5/1994 | Yalvac | G01N 21/75 |
| | | | 356/410 |
| 5,312,009 A | 5/1994 | Ratajczak et al. | |
| 5,334,348 A | 8/1994 | Saito et al. | |
| 6,055,487 A | 4/2000 | Margery et al. | |
| 6,277,646 B1 | 8/2001 | Guirguis et al. | |
| 6,485,438 B1 | 11/2002 | Minue | |
| 7,377,690 B1 * | 5/2008 | Diede | F42B 39/14 |
| | | | 102/364 |
| 7,758,815 B2 | 7/2010 | Hartselle | |
| 9,250,229 B2 | 2/2016 | Holmes | |
| 9,357,961 B2 | 6/2016 | Arefieg | |
| 9,417,210 B2 | 8/2016 | Arlen et al. | |
| 9,597,010 B2 | 3/2017 | Thompson et al. | |
| 2002/0009390 A1 * | 1/2002 | Lappe | B01L 3/502 |
| | | | 436/165 |
| 2005/0232638 A1 * | 10/2005 | Fucile | H04B 13/02 |
| | | | 398/140 |
| 2006/0008382 A1 * | 1/2006 | Salamitou | B01L 3/502715 |
| | | | 422/400 |
| 2007/0220798 A1 * | 9/2007 | Davidson | A01K 91/20 |
| | | | 43/4 |
| 2010/0155319 A1 * | 6/2010 | Felix | B01L 3/50215 |
| | | | 210/188 |
| 2011/0056276 A1 * | 3/2011 | Scott | G01N 21/15 |
| | | | 73/64.56 |
| 2011/0223673 A1 * | 9/2011 | Profitt | G01N 21/21 |
| | | | 436/8 |
| 2013/0030366 A1 | 1/2013 | Robertson et al. | |
| 2013/0284595 A1 * | 10/2013 | Lin | C12Q 1/006 |
| | | | 204/403.04 |
| 2015/0248833 A1 * | 9/2015 | Arne | G01D 21/00 |
| | | | 340/870.07 |
| 2015/0253321 A1 | 9/2015 | Chou et al. | |
| 2017/0267547 A1 * | 9/2017 | Miller | C02F 1/66 |
| 2020/0348662 A1 * | 11/2020 | Cella | G05B 23/024 |

FOREIGN PATENT DOCUMENTS

| | | |
|---|---|---|
| WO | WO2013170011 A2 | 11/2013 |
| WO | WO2016154262 A1 | 9/2016 |

OTHER PUBLICATIONS

Lee et al., "Ion-Sensitive Field-Effect Transistor for Biological Sensing," Sensors Sep. 2009, 9, 7111-7131.

Ahmed et al., "Biosensors for Hole-Cell Bacterial Detection," Clinical Microbiology Reviews, Jul. 2014, 27(3): 631-646.

Lan et al., "Recent advances in nanomaterial-based biosensors for antibiotics detection," Biosensors and Bioelectronics, vol. 91, May 2017, pp. 504-514.

English Translation of CN202776284U, Mar. 13, 2013 by Gao Feng.

* cited by examiner

Side view

FIG. 8

Top view

SMART PELLET FOR SAMPLE TESTING

FIELD OF THE INVENTION

The present invention relates to liquid (e.g., biological) sample testing techniques, and more particularly, to a submersible sensor device configured as a small pellet for testing biological and other liquid samples.

BACKGROUND OF THE INVENTION

Bioassays typically involve dipping a test strip into a liquid biological sample and then analyzing the test strip using a device such as a benchtop analyzer. However, in the time between sample collection and analysis, samples can become contaminated, degraded, or otherwise compromised. For instance, there might be a considerable amount of time between when a sample is collected from a patient and when the sample is analyzed. During that time the sample might be transported and/or stored before it reaches the testing site. All the while, the sample must be properly handled in order to maintain its integrity and usefulness for testing. Proper handling can include preventing contamination, leaking, maintaining the sample at a proper temperature to prevent degradation, etc. Thus, there are many opportunities for a sample to become compromised before it is tested.

Therefore, techniques that enable comprehensive testing of a sample upon collection would be desirable.

SUMMARY OF THE INVENTION

The present invention provides a submersible sensor device configured as a small pellet for testing biological and other liquid samples. In one aspect of the invention, a sensing device is provided. The sensing device includes: a housing; and one or more sensors contained within the housing, wherein the housing hermetically seals the sensors such that the sensing device is fully submersible in a liquid analyte.

In another aspect of the invention, another sensing device is provided. The sensing device includes: a housing; and one or more sensors hermetically sealed within the housing such that the sensing device is fully submersible in an analyte, wherein the housing includes a flat top surface and a flat bottom surface opposite the flat top surface, and wherein the flat top surface and the flat bottom surface are both circular such that the sensing device is shaped as a pellet having a diameter d of less than or equal to about 10 cm, and a thickness t of from about 1.25 mm to about 25 mm and ranges therebetween.

In yet another aspect of the invention, a method for analysis of a liquid sample is provided. The method includes: submerging a sensing device in the liquid sample, the sensing device including a housing, and one or more sensors contained within the housing, wherein the housing hermetically seals the sensors such that the sensing device is fully submersible in the liquid sample; collecting data from the liquid sample using the sensors; transmitting the data from the sensing device to at least one of a data management system and electronic records.

In yet another aspect of the invention, a system for analysis of a liquid sample is provided. The system includes: at least one sensing device having a housing, and one or more sensors contained within the housing, wherein the housing hermetically seals the sensors such that the sensing device is fully submersible in the liquid sample; and a data management system communicatively connected to the at least one sensing device.

A more complete understanding of the present invention, as well as further features and advantages of the present invention, will be obtained by reference to the following detailed description and drawings.

DETAILED DESCRIPTION OF PREFERRED EMBODIMENTS

Provided herein are improved techniques for point-of-collection sample testing using a submersible sensing device. The sensing device includes multiple sensors for sample analysis with integrated communication, power and identification (ID) components.

According to an exemplary embodiment, the sensing device is pellet-shaped and has small dimensions so that is can be easily submerged in a liquid sample that has been collected, e.g., from a patient. For testing, the device is simply dropped into a container such as a cup containing the sample. The device can operate with either major surface (top or bottom) resting against the bottom of the sample cup.

Preferably, the pellet is also thin so that only a minimum volume of sample is needed to submerse the pellet for testing.

By way of example only, according to one exemplary embodiment, the pellet-shaped device has a diameter d of less than or equal to about 10 centimeters (cm), preferably less than or equal to about 2.5 cm, and more preferably less than or equal to about 2 cm, e.g., from about 0.5 cm to about 1 cm and ranges therebetween. The thickness t of the device is preferably less than or equal to about 3 cm, more preferably less than or equal to about 0.5 cm, e.g., from about 1.25 millimeters (mm) to about 25 mm and ranges therebetween. The size of the device is important when testing is being performed on samples contained in standard-sized collection vessels or cups. For instance, sample testing for biologics such as for urinalysis often involve an analyte contained in a sample cup that has dimensions approximating 60 mm (diameter)×70 mm (height). Thus, in order for the pellet-shaped device to be placed in the sample cup with either its top or bottom surface resting fully on the bottom of the cup, the device itself must have a diameter that is smaller than the diameter of the sample cup. Further, since the device can work fine in either orientation with its top or bottom surface resting on the bottom of the sample cup, the smaller dimensions of the device (as compared to the sample cup) insure that when a user simply drops the device into the sample/sample cup the device will submerge in the sample and come to rest (with either its top or bottom surface) on the bottom of the sample cup.

As provided above, the pellet-shaped sensing device is equipped with a multitude of different sensors. The combination of sensors employed in a given one of the present sensing devices can vary depending on the target analyte. For instance, one set of sensors might be useful for collecting data from a biological sample, such as during urinalysis, whereas another different set of sensors might be better suited to testing a water sample or liquid chemical sample. The pellet-shaped sensing device can be configured accordingly. By way of example only, suitable sensors for use in the present sensing device include, but are not limited to, electrical sensors, electrochemical sensors, optical sensors, pressure sensors, temperature sensors, specific gravity sensors and/or acoustic sensors.

As provided above, the present pellet-shaped sensing device can have an integrated power component. For instance, the sensing device can be configured as a stand-alone device with an integrated battery source. This stand-alone configuration is especially beneficial for use in the field where an external power source might not be readily available. Alternatively, the sensing device can be part of an assembly that includes a system hub used to power the device, for example, via inductive charging. Use of such an assembly is well suited for environments with a constant power source, such as a hospital or doctor's office, laboratory, clinic, etc. Optionally, the integrated power component can be rechargeable via the system hub using direct connection to an external power source and/or via inductive charging. However, inductive charging can be used to power the device when the device itself does not have a self-contained integrated power component. Other power sources contemplated for use herein include, but are not limited to, a photovoltaic-based power supply such as a photovoltaic cell for generating power when under illumination, and a rechargeable battery for storing the energy generated by the photovoltaic cell.

Figure 1:
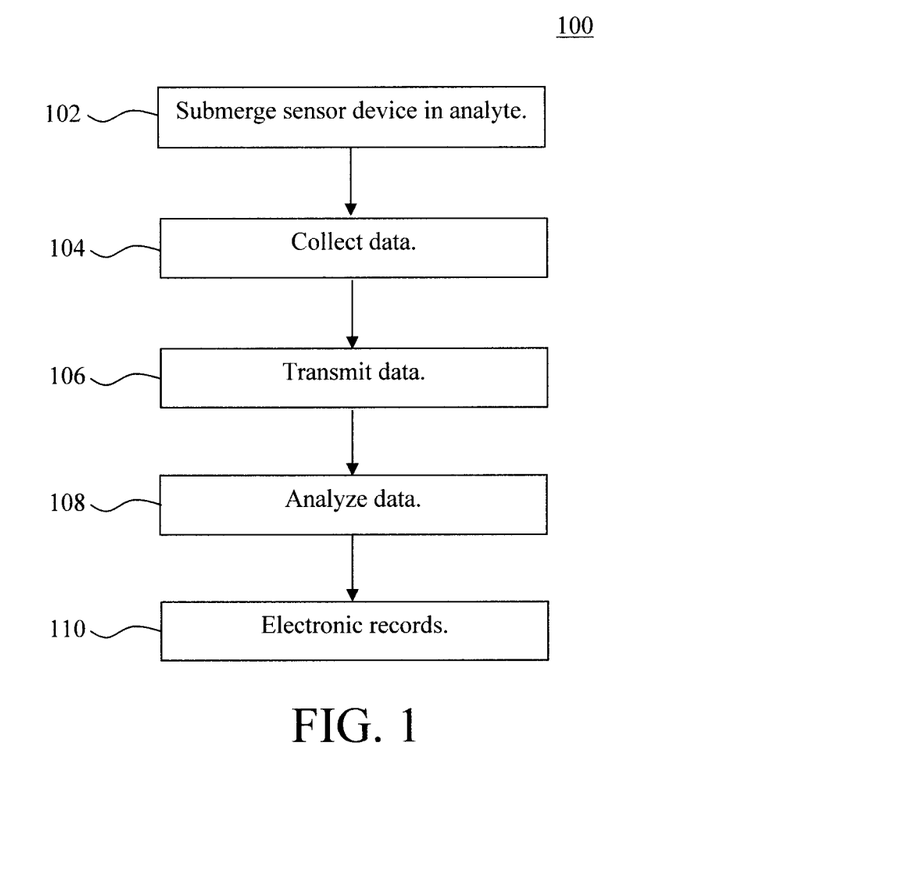
FIG. 1 is a diagram illustrating an exemplary methodology for analysis of a sample using the present pellet-shaped sensing device according to an embodiment of the present invention.

An overview of the present techniques is now provided by way of reference to methodology 100 of FIG. 1 for analysis of a sample using the present pellet-shaped sensing device. In step 102, the pellet-shaped sensing device is submerged in an analyte. Preferably the analyte is a liquid sample contained in a vessel or container such as a commercially available sample cup, and a volume of the analyte present in the cup is sufficient to fully submerge the sensing device in the analyte. By way of example only the analyte can be a biological sample such as for urinalysis, a water or liquid chemical sample such as for water or chemical testing, etc. As provided above, step 102 can be performed simply by dropping the pellet-shaped sensing device into the sample cup containing the analyte. The sensing device will be submerged in the sample as the sensing device comes to rest (with either its top or bottom surface) flat on the bottom of the sample cup. It is notable that while embodiments are described herein where the entire sensing device is fully submerged in the sample, it is also possible to obtain data from the sample if the surface(s) of the sensing device having the sensors (see below) are submerged in the analyte even if the entire pellet itself is not fully submerged. Thus for instance, if the volume of analyte is not sufficient to fully submerge the entire device, however the surface(s) of the device containing the sensors is submerged (i.e., the sensing surface(s) of the device are in the analyte), readings can be taken (even with the device only partially submerged).

Advantageously, testing can be performed at the point of collection of the sample thus preserving the integrity of the sample and data gleaned therefrom. For instance, a physician collecting a biological sample from a patient, a researcher collecting a water sample, etc. can collect the analyte sample (e.g., in a sample cup) and then immediately drop the pellet-shaped sensing device into the sample. By comparison, most conventional testing approaches involve benchtop equipment that is not suited for the field and thus oftentimes involve an extended period of time between when the sample is collected and when it is analyzed, during which time the sample is extensively handled such as during transport, shipping, etc.

In step 104 the pellet-shaped sensing device, now submerged in the analyte, is used to gather/collect data from the analyte. As provided above, the device can include a variety of different sensors (e.g., electrical sensors, electrochemical sensors, optical sensors, pressure sensors, temperature sensors, specific gravity sensors and/or acoustic sensors) configured to collect data from the analyte. The number and/or types of sensors present in the device can depend on the particular application and analyte being tested. For instance, certain biomarker sensors might be useful in evaluating a biological sample, however they would not apply in testing a water sample. Thus, according to an exemplary embodiment, different pellet-shaped sensing devices are available for different testing applications, varying from one another based on the particular sensors they include. In addition to gathering data from the analyte, information about the source of the sample may be recorded and associated with the other results. For example the patient identification (ID) may be added using a wireless link from a phone or other input device communicating with the pellet.

In step 106, the sensing device transmits the data it has collected. According to an exemplary embodiment, the data collected by the sensing device is transmitted to the cloud through a local hub and then to a data management system and/or electronic records such as electronic medical records or EMRs. See, for example, system 1100, described below. Preferably, data transmission from the pellet-shaped sensing device is performed wirelessly to enable the sensing device to be introduced into the analyte as a stand-alone unit.

However, embodiments are also anticipated herein where data is obtained from the pellet-shaped sensing device via a wired connection and/or collected and stored by the sensing device and subsequently transmitted to the system for archiving, analysis, etc.

The data transmitted from the sensing device can then be analyzed (step 108) and/or stored (archived) to create an electronic record (step 110). According to an exemplary embodiment, the data is processed via a data management system (see system 1100). As will be described in detail below, based on the data analysis a diagnostic report can be generated and transmitted to the appropriate user or users. For instance, for medical diagnostics analysis of the data collected from a patient sample (such as from urinalysis) can be transmitted to the doctor and/or hospital, clinic, etc, treating the patient. Similarly, analysis of data from a water sample can be transmitted to the laboratory, researcher, etc. conducting the testing.

Figure 2:
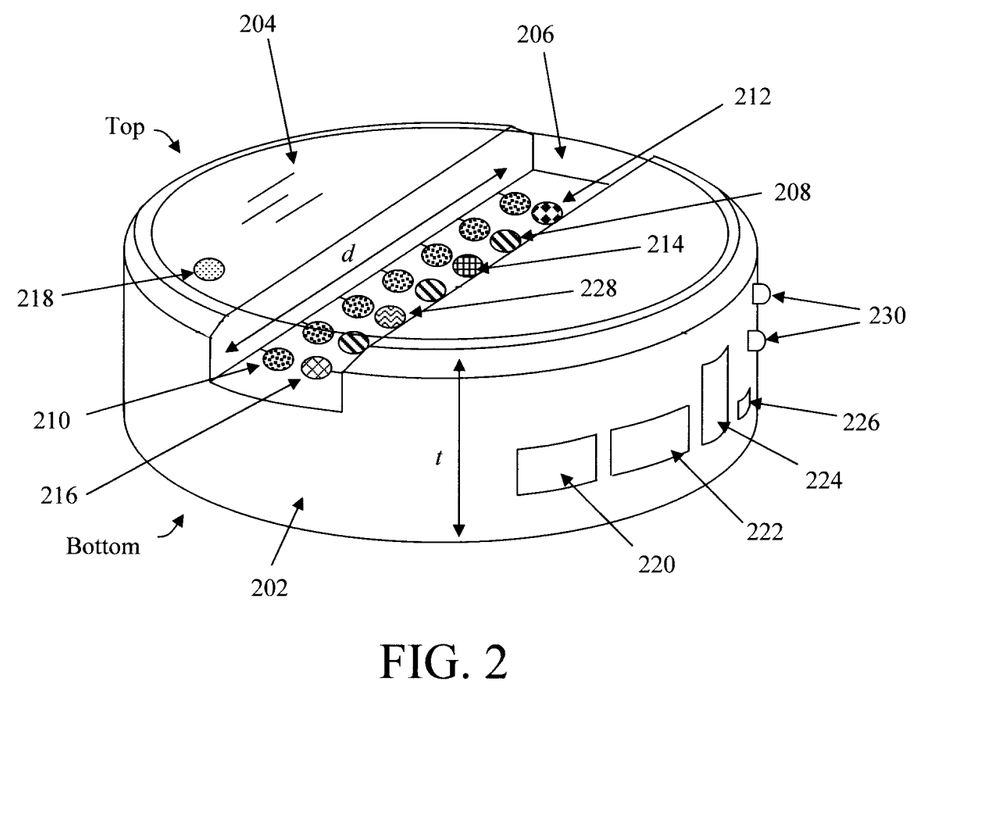
FIG. 2 is a diagram illustrating an exemplary configuration of the present pellet-shaped sensing device according to an embodiment of the present invention.

A more detailed description of the features of the present pellet-shaped sensing device is now provided by way of reference to the exemplary configuration of the device shown illustrated in FIG. 2. It is to be understood that the configuration, placement and/or type of sensors shown in FIG. 2 is merely an example provided to illustrate the device. Other configurations including different placement of the sensors and/or different types of sensors and form factor/housing are anticipated herein.

As shown in FIG. 2, the sensing device is preferably pellet-shaped. By "pellet-shaped" it is meant that the device has a cylindrical shape with circular, flat top and bottom surfaces on opposite ends thereof. As provided above, during use the device is simply dropped into the liquid sample and, e.g., comes to rest (either on its top or bottom surface) at the bottom of the container containing the sample. For use in testing samples in standard sized sample cups, the pellet preferably has a small diameter d and thickness t. Exemplary values for d and t were provided above. The overall size and shape of the sensing device is largely dictated by the shape of the housing 202 used to form the device. See FIG. 2. For instance, according to an exemplary embodiment, the sensing device includes a pellet-shaped housing 202 (of the size, shape and dimensions provided above) containing one or more sensors. In order for the device to be submersible, the housing 202 is water-tight, hermetically-sealing the sensors and other electronic components of the device from the outside analyte. Suitable housing materials include, but are not limited to, plastic, metal, polymer, and other materials. For instance, the housing 202 can be formed from an injection molded plastic. In cases where the sensors protrude from the housing 202, a sealant (such as a polymer adhesive) is used to seal around the sensor portion that penetrates the housing 202. However, not all of the sensors need to pass through the housing 202. For instance, optical measurements may be made through the housing, as long as the housing is transparent (in part or in whole). Thus, embodiments are contemplated herein wherein at least a part of the housing 202 is transparent. For instance, the entire housing 202 can be made from a transparent material or, alternatively, portions (e.g., transparent windows) can be created in the housing 202 at the location(s) of the optical sensors.

Microfluidics can be used to collect a unitized amount of sample from the analyte to the sensing surface. For instance, the sensing device can include an absorbent pad 204 on at least one surface thereof covering the sensors (see for example FIG. 2). Suitable absorbent pad materials include, but are not limited to, a cellulose material such as paper, cotton, cloth, polymer membrane and hydrogel, etc. In the present example, the absorbent pad 204 is located on the top surface of the pellet over the sensors. The pad 204 is configured to adsorb a specified volume of liquid. Thus, measurements made can be analyzed based on that specific volume of analyte collected by the absorbent pad 204. By way of example only, the absorbent pad 204 is intended for a single use and is replaced after testing has completed. Additionally, locating one or more of the sensors within a channel 206 on the surface of the device ensures that (based on the dimensions of the channel 206) that a unitized volume of the analyte is contacted with the sensing surface. See, for example, FIG. 2 where one or more of the sensors are located in channel 206 on the top surface of the sensing device. To define the channel 206, a cover slip may be used in place of the absorbent pad 204.

Figure 3:
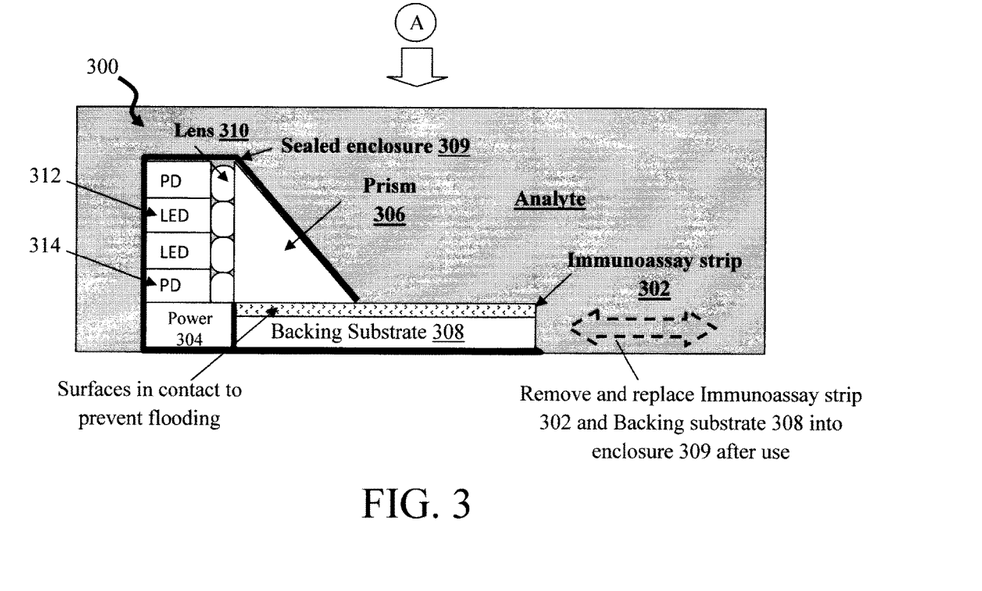
FIG. 3 is a side-view diagram illustrating an exemplary immunoassay optical detector that may be used in the present pellet-shaped sensing device according to an embodiment of the present invention.

In the present example, the pellet-shaped optical sensor includes at least one optical sensor 208 on a surface thereof. Optical sensors are useful, for example, in applications involving color detection such as immunoassays and/or applications where determining the color of the analyte is needed immunoassays, for example, are biochemical tests that can be read using observable color changes based on the reagents. Additives, impurities, etc. present in a water sample might affect its color which can be detected using an optical sensor 208. An exemplary optical sensor that may be used in accordance with the present techniques is shown in FIG. 3—described below.

The device shown in FIG. 2 also includes at least one electrochemical sensor 210 on a surface thereof. An electrochemical sensor uses a working electrode and a reference electrode to measure the electrical parameters of reactants in a solution. For biologics, for example, the reactants can include known biomarkers for various conditions, diseases, etc. See, for example, Adhikari et al., "Carbon Nanomaterials Based Electrochemical Sensors/Biosensors for the Sensitive Detection of Pharmaceutical and Biological Compounds," Sensors September 2015, 15, 22490-22508, the contents of which are incorporated by reference as if fully set forth herein. Suitable electrochemical sensors include, but are not limited to, glucose sensors available, for example, from Dexcom, Inc., San Diego, Calif. and Medtronic, Dublin, Ireland, and i-STAT® sensors available from Abbott, Princeton, N.J.

The present exemplary configuration also includes at least one pressure sensor or strain gauge 212 on a surface of the device. A pressure sensor or strain gauge can be used to obtain density measurements of the analyte in order to determine certain parameters such as specific gravity. Suitable pressure sensors are commercially available, for example, from First Sensor, Berlin, Germany. An exemplary strain gauge and techniques for determining specific gravity are described in conjunction with the description of FIGS. 8-10, below.

An acoustic sensor 214 can also be integrated into the design. As will be described below, an acoustic sensor can be used in assessing the height of the liquid analyte above the strain gauge (e.g., based on time of flight of an acoustic wave). Suitable acoustic sensors include, but are not limited to, the surface acoustic wave (SAW) sensors available, for example, from the EV Group, Austria.

An ion-sensitive field effect transistor (FET) sensor 216 on a surface of the sensing device is also part of the design in this example. An ion-sensitive FET can be used to determine the pH of the analyte. For instance, an ion-sensitive FET can measure the concentration of $H^+$ or $OH^-$ ions in a solution based on an interface potential formed on the gate insulator. See, for example, Lee et al., "Ion-Sensitive Field-Effect Transistor for Biological Sensing," Sensors September 2009, 9, 7111-7131, the contents of which are incorporated by reference as if fully set forth herein.

Other sensors may also be included to monitor the sample quality such as temperature, contaminants, etc. Sample temperature is monitored using a temperature sensor 218. As will be described in detail below, temperature measurements are also useful in specific gravity calculations. The notion regarding contaminants is that one wants to remove any possible interference in the data from contaminants such as bacteria and/or chemicals found for example in medications, and to initiate an (e.g., audible) alarm if contaminants are detected.

The method of contaminant detection depends on the type of analytic. It can involve optical sensors measuring a change in fluorescence or, less commonly, in absorbance or luminescence of the biosensor surface upon analyte recognition. It can also be electrical, such as impendence or electro chemical sensors to measure the change in impedance or potential or current upon the binding of the analyte to surface or redox reaction. An exemplary process for bacteria detection is described, for example, in Ahmed et al., "Biosensors for Hole-Cell Bacterial Detection," Clinical Microbiology Reviews, July 2014, 27(3): 631-646, the contents of which are incorporated by reference as if fully set forth herein.

For medications such as antibiotics, conventional methods of detection such as chromatography, capillary electrophoresis (CE), diode array (DA), flame ionization (FI), and enzyme-linked immunosorbent assay (ELISA) all involve complicated processes. However, nanoparticle based optical and electrochemical sensors may instead be employed. See, for example, Lan et al., "Recent advances in nanomaterial-based biosensors for antibiotics detection," Biosensors and Bioelectronics, vol. 91, May 2017, pgs. 504-514, the contents of which are incorporated by reference as if fully set forth herein.

As shown in FIG. 2, the sensing device includes a variety of self-contained electronics. For instance, a miniature battery 220 is used to power the device and sensors as well as data transfer operations. A microcontroller 222 or system-on-a-chip provides the device with on-board processing and memory capabilities. The sensing device has Bluetooth® 224/RFID 226 enabled connectivity which enables the transfer of data for example to the cloud then to a data management system and/or electronic medical records (EMRs). All data collected by the device will be time-stamped and dated. A global positioning system (GPS) chip can be incorporated to provide location information. Location information can also be incorporated by coupling with users GPS devices, such as a smartphone/or watch.

Preferably, the sensing device can detect when it is added to (or removed from) a liquid sample so that it knows when to start (or complete) an analysis. For instance, an accelerometer 228 can detect the motions associated with the pellet being dropped into a liquid sample and subsequently being retrieved from the sample. A variety of suitable accelerometer and other motion sensors are commercially available, for example, from PCB®, Depew, N.Y. As shown in FIG. 2, status light emitting diodes (LEDs) 230 are also present on the device surface to indicate when analysis is underway, completed, etc.

One type of optical sensor contemplated for use in the present sensing device is an immunoassay optical detector 300. See, for example, FIG. 3 (side view) and FIG. 4 (top-down view). As provided above, an immunoassay is a biochemical test that can be read using observable color changes. Thus, in the present example, an immunoassay test strip ("immunoassay strip") is combined with an optical sensor configured to detect the resulting color changes when the sensor is immersed in the analyte.

Referring for instance to FIG. 3, immunoassay optical sensor 300 includes an immunoassay strip 302, light source(s), light detector(s) and associated power source 304, a prism 306 (or other means) for directing light from the light source(s) toward the immunoassay strip 302 and back to the detectors, and a backing substrate 308. In the configuration shown, it is important that the bottom surface of the prism 306 and the immunoassay strip 302 be in intimate contact with each other so that the fluid being tested "wicks" in along the immunoassay strip 302 and does not "flood" the surface. If the surface is "flooded," the reagents can be excessively diluted, mixed or washed away by the excess liquid. On the bottom of the prism, an optional aperture 410 (see FIG. 4—described below) can be installed to limit the scattered light interference.

As shown in FIG. 3, the sensor 300 is encased in a sealed (water-tight) enclosure 309 with an opening at the bottom of the prism 306 for insertion/removal of the immunoassay strip 302. This enables the immunoassay strip in sensor 300 to be easily removed after use, and replaced with a new strip.

Figure 4:
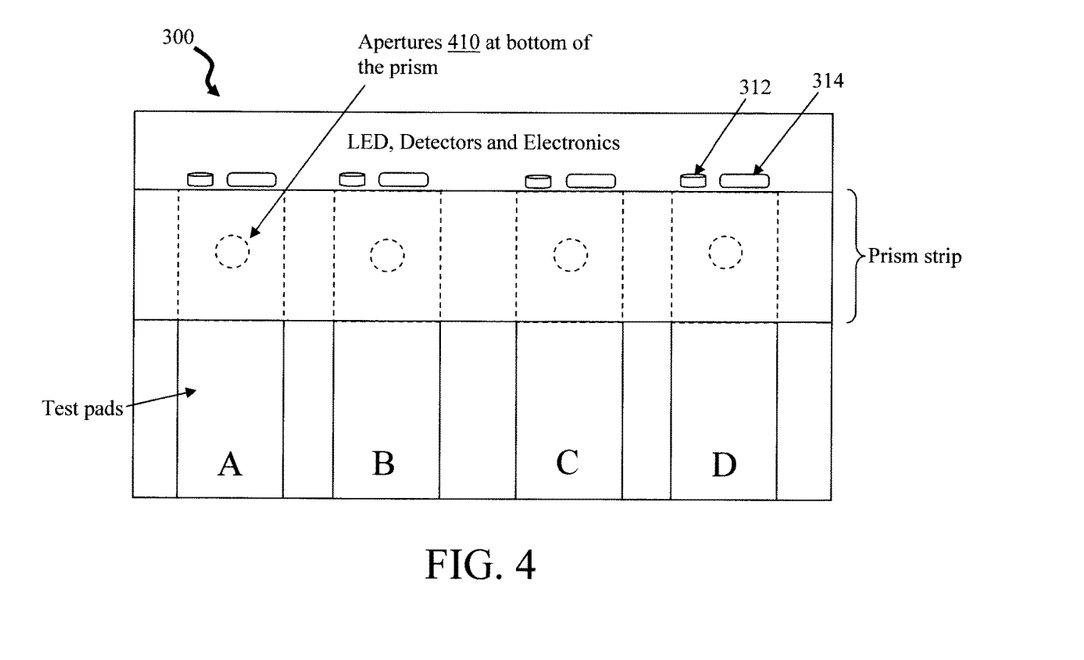
FIG. 4 is a top-down diagram illustrating the immunoassay optical detector according to an embodiment of the present invention.

Generally, an immunoassay strip is formed from a porous material and, via capillary action, an analyte sample is transported laterally across the strip. The capillary action is used to limit fluid volume and avoid excessive dilution of the reagents. As the sample moves across the strip it contacts one or more areas containing certain reagents that react with the analyte (or absent the corresponding analyte do not react) forming a complex. Accumulation of the complexes changes a color of the strip. The strip can include multiple lanes or test pads. See FIG. 4 where the immunoassay strip has, e.g., 4 test pads A-D. FIG. 4 is a top-down view, e.g., from viewpoint A (see FIG. 3). As provided above, after use the immunoassay strip in sensor 300 can easily be removed and replaced with a new strip. As shown in FIG. 4, apertures 410 can be installed at the bottom of the prism 306 in order to limit the scattered light interference. By way of example only, the apertures might be installed on the bottom of the prism 306 simply by affixing a light blocking layer to the bottom of the prism 306 with the apertures 410 present in the light blocking layer.

In order to illuminate the immunoassay strip, at least one light source 312 is provided. At least one light detector 314 is used to detect the light reflected off of the immunoassay test strip 302. Optionally, lenses 310 can be employed between the light source(s) 312/light detector(s) 314 and the prism 306 to focus the light. In this particular example, the light source(s) are LEDs, and the light detectors are photo-detectors, such as photodiodes (PD). CCD/CMOS imager can also be used as light detectors. Thus, according to an exemplary embodiment, LEDs are used as a light source and photodiodes (PD) are used as light detectors in optical sensor 300, e.g., with the LEDs generating light to illuminate the immunoassay test strip and the photodiodes detecting the light reflected off of the immunoassay test strip. In the exemplary configuration shown in FIG. 3, the LEDs/photodiodes are positioned orthogonal to the immunoassay test strip 302, and light to/from the LEDs/photodiodes and the immunoassay strip 302 is guided using prism 306 (or other suitable means such as a mirror) located in between the LEDs/photodiodes and the immunoassay test strip 302.

Figure 5:
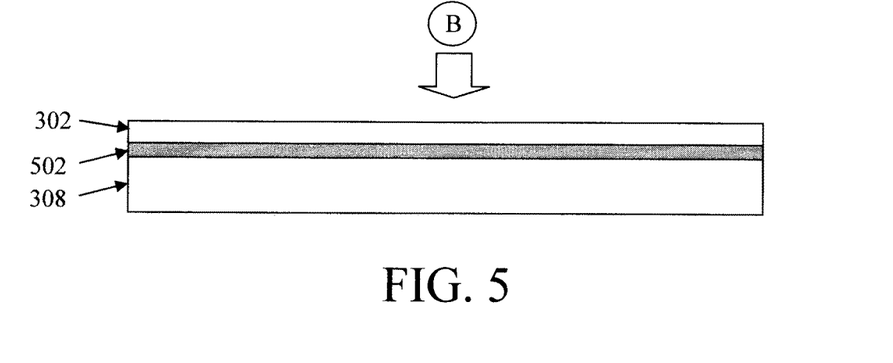
FIG. 5 is a cross-sectional diagram illustrating a superabsorbent polymer (SAP) layer under an immunoassay strip of the optical detector according to an embodiment of the present invention.
Figure 6:
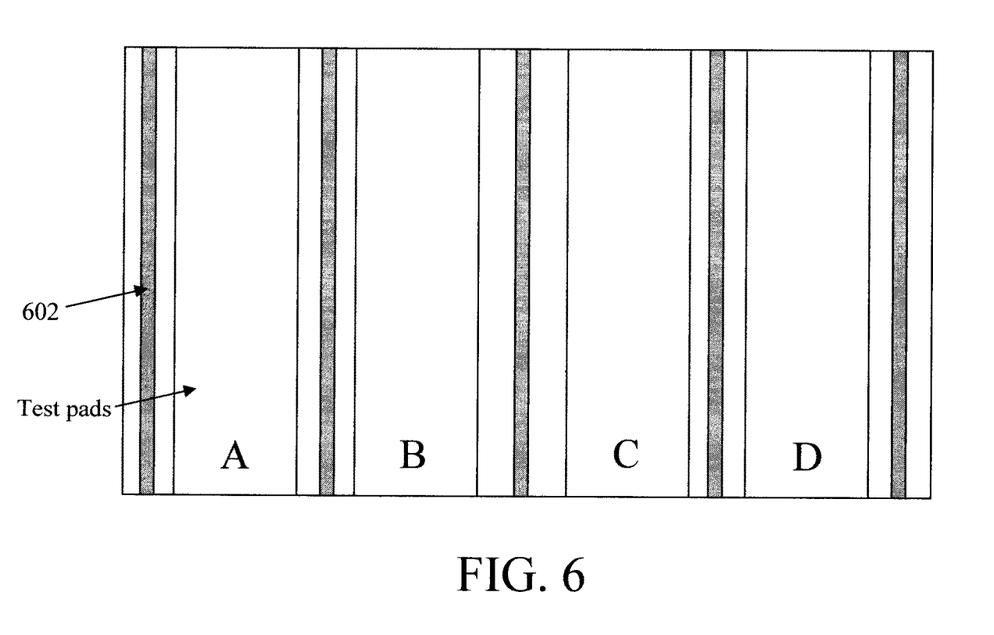
FIG. 6 is a top-down diagram illustrating separators being employed between test pads on the immunoassay strip according to an embodiment of the present invention.

The amount of the liquid analyte on each of the test pads should be controlled and limited to ensure the accuracy and avoid cross contamination between the test pads. There are several ways to do this. One example is to build separators between each test pad. See FIGS. 5 and 6. Another example is to have the separators as a part of the sensor 300 (not shown) which are engaged to make contact in between the test pads to isolate the test pads, when the immunoassay strip 302 is inserted into sensor 300 and wetting is detected (i.e., the separators can be configured to swell when wet, thereby engaging the immunoassay strip 302). The separators can also be built on the test pads as well (see, e.g., separators 602 in FIG. 6). In one example, the separators are made of a material that swells (i.e., expands) when wet, such as a superabsorbent polymer (SAP). One example of the SAP is sodium polyacrylate. Another example of the SAP is hydrogel. FIG. 5 depicts a cross-section view of the immunoassay strip 302 with a SAP layer 502 present between the immunoassay strip 302 and the backing substrate 308. As shown in FIG. 6, there are also separators 602 (e.g., SAP strips) in between the test pads on the upper surface of the immunoassay strip 302 to serve as a separation wall when the immunoassay strip 302 is wet. During use, liquid wicks through the immunoassay strip 302 and wets the SAP layer 502 and separators 602/SAP strips. The SAP swells and raises the immunoassay strip 302 to contact the bottom surface of the prism 306 to seal the test pads (i.e., as provided above, the bottom surface of the prism 306 and the immunoassay strip 302 should be in intimate contact with each other so that the fluid being tested "wicks" in along the immunoassay strip 302 and does not "flood" the surface). FIG. 6 is a top-down view, e.g., from viewpoint B (see FIG. 5).

Figure 7:
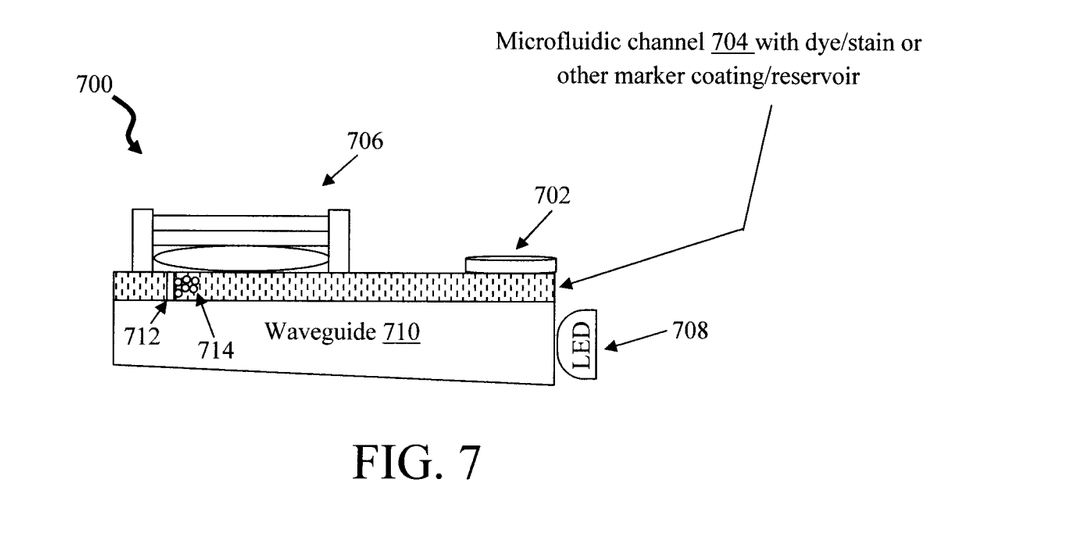
FIG. 7 is a diagram illustrating an exemplary microscope component that may be used in the present pellet-shaped sensing device according to an embodiment of the present invention.

Another type of optical sensor contemplated for use in the present sensing device is a microscope component 700. See FIG. 7. As shown in FIG. 7, the microscope component 700 includes an inlet 702 for analyte to enter the microscope component 700 at one end of a microfluidic channel 704 and an imaging device 706 on an opposite end of the microfluidic channel 704. The liquid analyte is either driven by capillary force or by a pump that is connected to the microfluidic channel 704. A light source 708 (adjacent to the inlet 702 end of the microfluidic channel 704) is provided with means such as a waveguide 710 (beneath the microfluidic channel 704) to direct light from the light source 708 to the imaging device 706.

According to an exemplary embodiment, the microfluidic channel 704 is coated with a dye, stain, and/or other type of marker specific for one or more reagents. As the analyte enters the microscope component 700 through the inlet 702 and passes through the microfluidic channel 704 the reagents, if present in the analyte, will react with the markers. This reaction (or lack thereof) is then captured in an image via the imaging device 706. For instance, reaction of a stain or dye with a particular reagent will cause a particular color or other indicia to be present in the image. According to an exemplary embodiment, a membrane 712 is installed at an end of the microfluidic channel 704 proximal to the imaging device 706 to collect particle sediment 714 in the sample while allowing liquid to pass. Microscope component 700 (via the imaging device 706) can take images of the sediment for further analysis.

According to an exemplary embodiment, the imaging device 706 is a charge-coupled device/complementary metal oxide semiconductor CCD/CMOS imager. Suitable CCD/CMOS imaging devices include, but are not limited to the Omnivision OV6922 2.5 micrometer (μm) pixel size camera on a chip available from OmniVision Technologies, Inc., Santa Clara, Calif. Any suitable light source may be employed in the microscope component 700. According to an exemplary embodiment, the light source is an LED light source. See FIG. 7. By way of example only, the LED light source can include a broad band, white light LED, a narrow band single wavelength LED, or a combination of multiple narrow band LEDS.

The exemplary imaging device described immediately above is a high-resolution optic that enables component 700 to detect the presence of microscopic particles in the sediment 714. For instance, in the context of a patient sample submitted, e.g., for urinalysis, microscope component 700 can be used to detect and quantify white blood cells, red blood cell casts, epithelial cells, hyaline casts, crystals, etc. by looking at color, shape, and relevant features for the different cell types.

Figure 8:
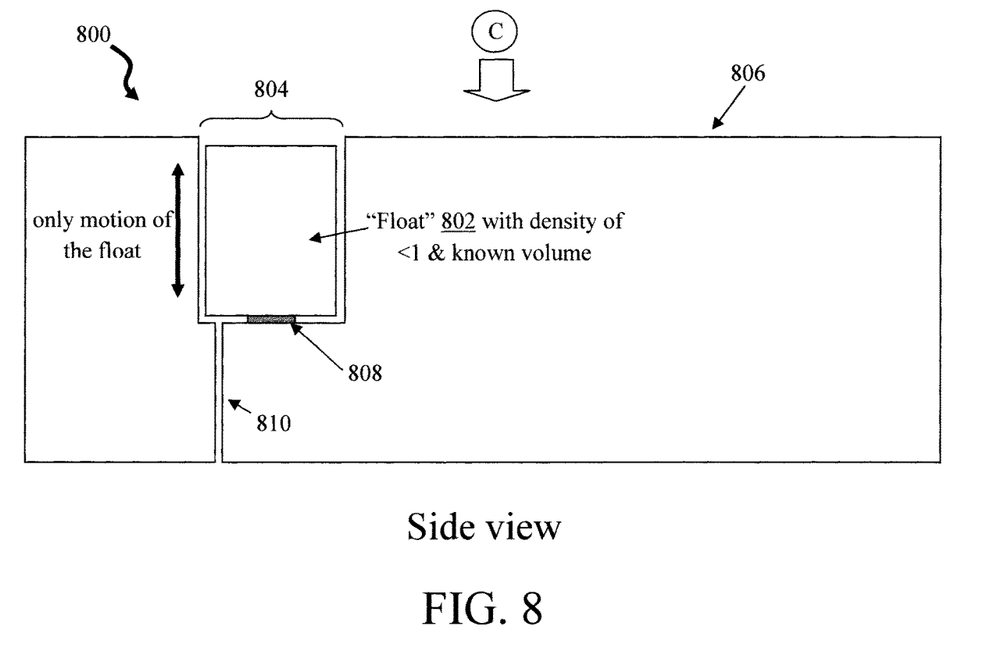
FIG. 8 is a side-view diagram illustrating an exemplary strain gauge that may be used in the present pellet-shaped sensing device according to an embodiment of the present invention.

As provided above, the present sensing device can include a strain gauge. A strain gauge is employed to obtain useful measurements such as specific gravity from an analyte. An exemplary strain gauge 800 is shown illustrated in FIG. 8 (side view) and FIG. 9 (top view). Referring first to FIG. 8, strain gauge 800 includes a float 802 positioned within a cavity 804 in the gauge housing 806. The float 802 is in contact with a strain sensor 808 at the bottom of the cavity 804. Further, as shown in FIG. 8, the float 802 is preferably recessed below a top surface of the gauge housing 806 to prevent the float 802 from being physically depressed for instance by the bottom of the sample cup should the sensing device (when placed in the analyte) settle with its top major surface facing down (see above).

Also with regard to the sensing device being operable in either orientation, a vent line 810 is provided leading from the bottom of the cavity 804 out to an opposite side of the gauge housing 806 (from the cavity 804). That way, should the sensing device land upside down in the analyte then air can be easily dispelled from the cavity 804 through the vent line 810. Suitable strain sensors include, but are not limited to, microelectromechanical (MEMs) sensors available, for example, from the Amphenol Corporation, Wallingford, Conn.

Figure 9:
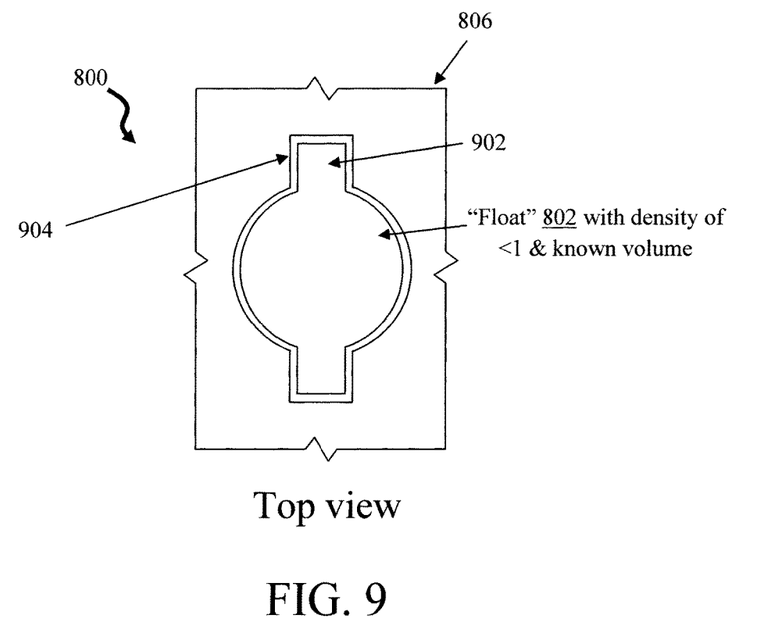
FIG. 9 is a top-down diagram illustrating the strain gauge according to an embodiment of the present invention.

FIG. 9 provides a top view of strain gauge 800 (for example from view point C—see FIG. 8). As shown in FIG. 9, the float 802 preferably has a shape that prevents twisting of the float 802 relative to the gauge housing 806. In other words, the shape of the float 802 (and complimentary shape of the cavity 804) is such that the only motion of the float 802 is up and down within the cavity 804. See FIG. 8. That way a more accurate strain measurement based on specific gravity of the analyte can be obtained. By way of example only, as shown in FIG. 9 the float 802 can be configured with a protrusion(s) 902 that compliment a vertical track(s) 904 along the wall of the gauge housing 806. That way, any twisting or rotation of the float 802 is prevented, while permitting the float 802 to freely move up and down.

According to an exemplary embodiment, the float 802 has a known density of less than 1 and is of a known volume. Since the density and volume of the float 802 are known, specific gravity of the analyte can be calculated from the buoyancy force on the strain sensor 800. With a known temperature value of the analyte (via a temperature sensor—see above), corrections can be made for thermal expansion of the fluid. It is notable that the sign of force is reversed if the sensing device is upside down in the analyte.

Figure 10:
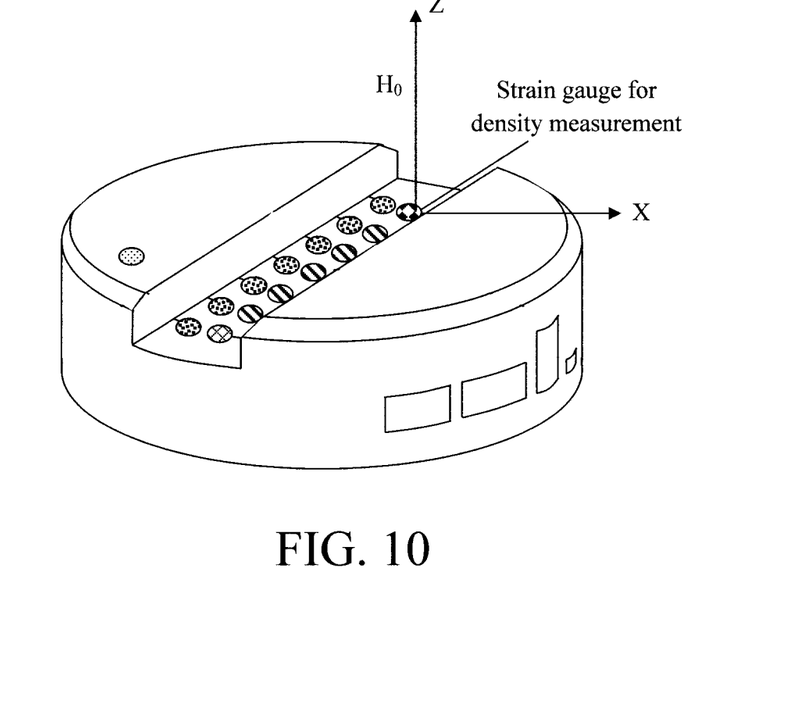
FIG. 10 is a diagram illustrating the height $H_0$ of the liquid analyte above the strain gauge according to an embodiment of the present invention.

An exemplary process for calculating the specific gravity of an analyte is now described by way of reference to FIG. 10. The sensing device shown in FIG. 10 includes a strain gauge that can be configured as described in accordance with the description of FIGS. 8 and 9, above. Based on the pressure P reading from the strain gauge the following calculation can be made:

$$P(t) = H(t) A_s \rho(t), \quad (1)$$

wherein H (t) is the height of the liquid analyte above the strain gauge in the sample cup (see for example FIG. 10), $A_s$ is the area of the strain gauge, and ρ(t) is the density of the liquid analyte. The height of the liquid analyte above the strain gauge can be measured by time of flight of an acoustic wave (using, e.g., an acoustic sensor—see above), or by an accelerometer and gyrometer that are triggered when the pellet-shaped sensor device is wet when dropping into the sample cup. If the device lands upside down in the sample cup or tilted, the thickness of the pellet-shaped sensor device will be corrected from the measurement.

Absent medical conditions, urinalysis for adults normally has a specific gravity of from about 1.000 to about 1.030. However, there is an increased specific gravity associated with certain medical conditions such as dehydration, excessive sweating, decreased blood flow to kidneys, etc. Conversely, there is a decreased specific gravity associated with other medical conditions such as renal failure, interstitial nephritis, etc. Thus, based on the determination made using Equation 1 above, it can be determined whether the specific gravity of a particular analyte (namely the ratio of the density of the liquid analyte ρ(t) calculated from the sensor readings as per Equation 1, above, to density readings of adults without a medical condition as a reference) indicates the existence of a medical condition (i.e., the analyte has a specific gravity that is outside of the norm) and, if so, what type of condition it might or might not be (e.g., a high specific gravity can exclude those conditions that cause a low specific gravity and vice versa).

Figure 11:
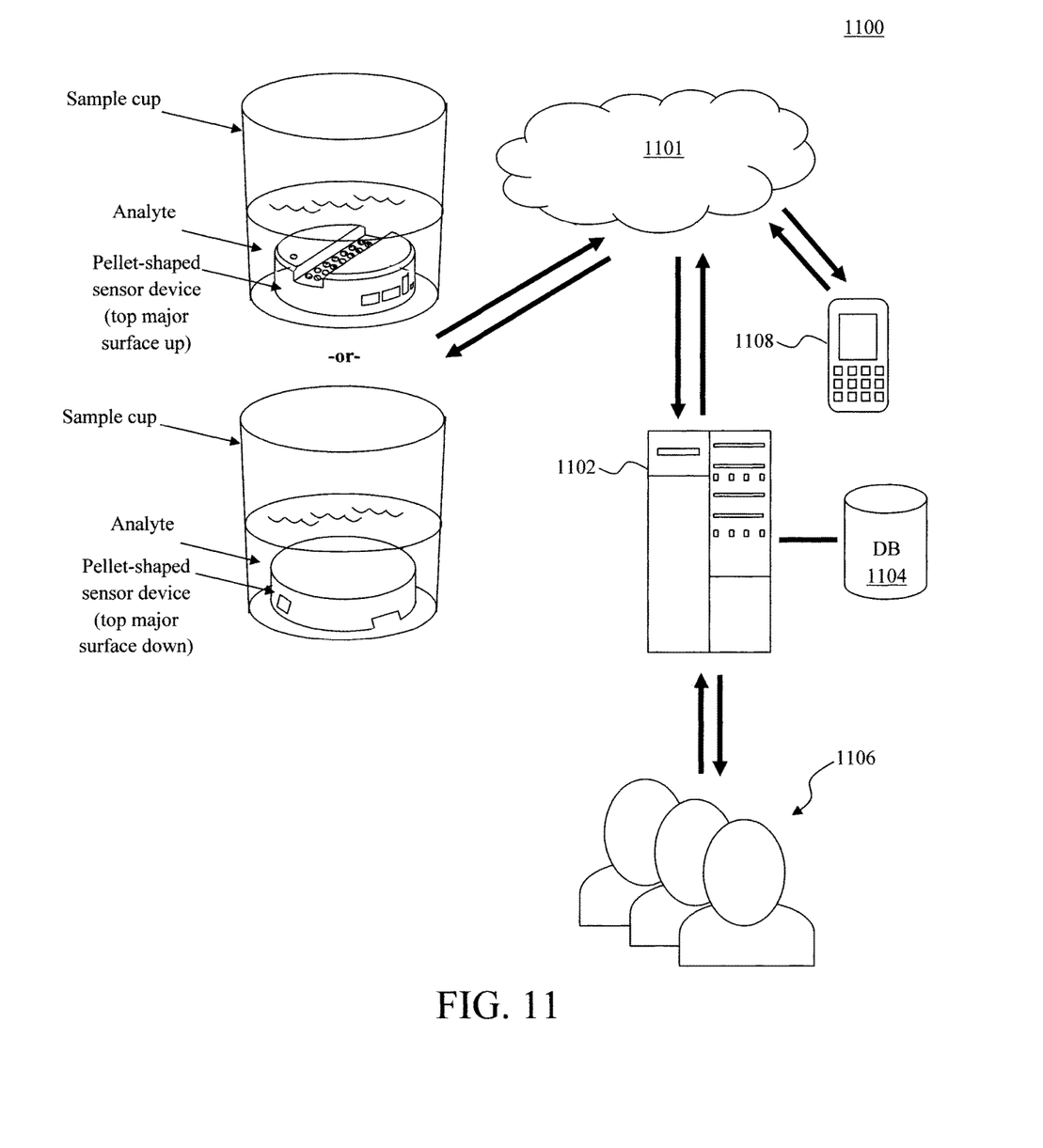
FIG. 11 is a diagram illustrating an exemplary system for analysis of a sample using the present sensing device according to an embodiment of the present invention.

FIG. 11 is a diagram illustrating an exemplary system 1100 for analysis of a sample using the present sensing device. As shown in FIG. 11, the system 1100 includes at least one pellet-shaped sensing device in communication with a data management system 1102 (via cloud 1101). Data management system 1102 is configured to receive the data collected by the sensing device(s), process/analyze the data, and generate electronic records such as EMRs stored, for example, in a database DB 1104.

As shown in FIG. 11, data management system 1102 can also be accessed by one or more interested entities 1106. For instance, when the sample analyte is collected from a patient, interested parties can include the doctor and/or hospital, clinic, etc, treating the patient. In a research or diagnostic setting such as water sample testing, interested parties can include the laboratory and/or researcher, water authority and/or municipality from where the samples were collected, etc. Optionally, the system 1100 can also permit communication between the sensor device and/or data management system 1102 (via cloud 1101) with one or more local devices 1108 such as a smartphone or other mobile, smart devices through which users (such as the patient and/or other interested parties—see above) can annotate the data collected by the sensing data. Upon receiving the data from the pellet-shaped sensor device, doctors for instance can add notes related to observations, diagnosis, recommended further testing, etc. A patient might provide identifying data for themselves (e.g., patient data such as name, date of birth, height, weight, etc.) and/or a description of health conditions, diet, symptoms they are experiencing, etc.

FIG. 11 also illustrates how the present pellet-shaped sensing device can be submerged in a sample with either its major top or bottom surfaces facing up or down. For instance, in the top depiction, the pellet-shaped sensing device is submerged rightside up in the analyte, whereas in the bottom illustration it is upside down. Either orientation (rightside up or upside down) is suitable. Further, it is notable that the orientation of the sensing device (either rightside up or upside down) flat against the bottom of the sample cup is needed in particular when the above-described (see, e.g., FIGS. 8 and 9) strain gauge 800 is being employed for measurement. On the other hand, if the strain gauge 800 is not being read then the pellet-shaped sensing device can work in any orientation in the fluid sample, including tilted or sideways.

As provided above, once the device is submerged in the analyte, it collects data via its multiple sensors, and transmits that data (e.g., wirelessly) to data management system 1102. The data collected from the sensing device by data management system 1102 via cloud 1101 can then be analyzed and/or stored as an electronic record in database 1104. By way of example only, data collected from a patient sample for urinalysis might be analyzed collectively from all of the sensors to determine whether the patient has biomarkers or other indicators for known conditions. The measurement from multiple sensors can also be used to calculate the correction of interference. For instance, pH effect on glucose can be corrected with known pH. For instance, urinalysis biomarkers can include pH, specific gravity, leucocytes, nitrate, protein, glucose, ketones, urobilinogen, bilirubin, and blood, and may also include other biomarkers for sepsis/inflammation, bacterial speciation, tumor markers, and fibril aggregation. Also, for example, machine-learning particle recognition algorithms can be applied to urinalysis samples and new data used to further train and improve visual analytics of the image data captured by the optical sensors. Interested parties 1106, e.g., doctors, researchers, etc. can access the data and/or data analysis.

Figure 12:
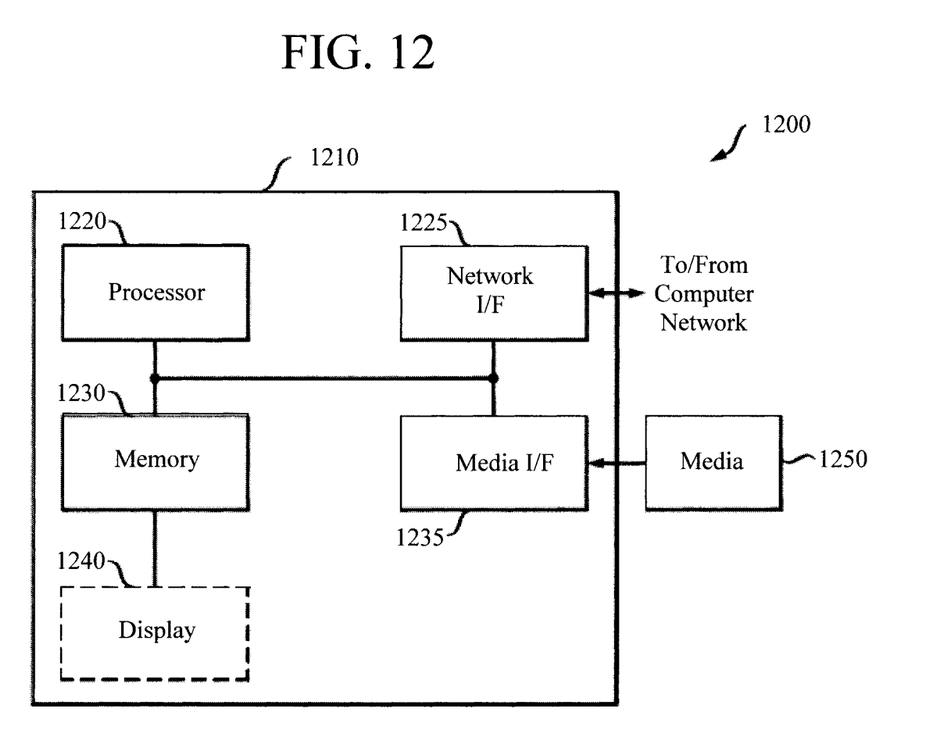
FIG. 12 is a diagram illustrating an exemplary apparatus that can be configured to implement one or more of the methodologies presented herein according to an embodiment of the present invention.

Turning now to FIG. 12, a block diagram is shown of an apparatus 1200 that can be configured to perform one or more of the methodologies presented herein. For example, apparatus 1200 can serve as the data processing apparatus 1102 in system 1100 and can be configured to perform one or more of the steps of methodology 100 (of FIG. 1) described above. Apparatus 1200 includes a computer system 1210 and removable media 1250. Computer system 1210 includes a processor device 1220, a network interface 1225, a memory 1230, a media interface 1235 and an optional display 1240. Network interface 1225 allows computer system 1210 to connect to a network, while media interface 1235 allows computer system 1210 to interact with media, such as a hard drive or removable media 1250.

Processor device 1220 can be configured to implement the methods, steps, and functions disclosed herein. The memory 1230 could be distributed or local and the processor device 1220 could be distributed or singular. The memory 1230 could be implemented as an electrical, magnetic or optical memory, or any combination of these or other types of storage devices. Moreover, the term "memory" should be construed broadly enough to encompass any information able to be read from, or written to, an address in the addressable space accessed by processor device 1220. With this definition, information on a network, accessible through network interface 1225, is still within memory 1230 because the processor device 1220 can retrieve the information from the network. It should be noted that each distributed processor that makes up processor device 1220 generally contains its own addressable memory space. It should also be noted that some or all of computer system 1210 can be incorporated into an application-specific or general-use integrated circuit.

Optional display 1240 is any type of display suitable for interacting with a human user of apparatus 1200. Generally, display 1240 is a computer monitor or other similar display.

Although illustrative embodiments of the present invention have been described herein, it is to be understood that the invention is not limited to those precise embodiments, and that various other changes and modifications may be made by one skilled in the art without departing from the scope of the invention.

What is claimed is:

1. A sensing device, comprising: a housing; and sensors comprising two or more types of sensors contained within the housing, wherein the housing hermetically seals the sensors such that the sensing device and the sensors are fully submersible in a liquid analyte, wherein the sensing device once submerged in the liquid analyte is configured to collect data via the sensors and transmit the data, and wherein the sensors comprise at least one strain gauge comprising:
    a sensor housing having a cavity therein; a strain sensor on a bottom of the cavity; a float positioned within the cavity in contact with the strain sensor; and
    at least one optical sensor comprising: an immunoassay test strip.

2. The sensing device of claim 1, wherein the housing comprises a flat top surface and a flat bottom surface opposite the flat top surface, and wherein the flat top surface and the flat bottom surface are both circular such that the sensing device is shaped as a pellet.

3. The sensing device of claim 2, wherein the pellet has a diameter d of less than or equal to about 10 cm.

4. The sensing device of claim 3, wherein the diameter d is less than or equal to about 2 cm.

5. The sensing device of claim 4, wherein the diameter d is from about 0.5 cm to about 1 cm and ranges therebetween.

6. The sensing device of claim 2, wherein the pellet has a thickness t of from about 1.25 mm to about 25 mm and ranges therebetween.

7. The sensing device of claim 1, wherein at least a portion of the housing is transparent.

8. The sensing device of claim 1, wherein the two or more types of sensors comprise sensors selected from the group consisting of: electrical sensors, electrochemical sensors, optical sensors, pressure sensors, temperature sensors, specific gravity sensors, acoustic sensors, and combinations thereof.

9. The sensing device of claim 1, wherein the at least one optical sensor comprises the immunoassay test strip on a backing substrate; a light source; a light detector, wherein the light source and light detector are oriented orthogonal to the immunoassay test strip: and a prism between the immunoassay test strip and the light source and light detector.

10. The sensing device of claim 9, wherein the light source comprises a light emitting diode and the light detector comprises a photodiode.

11. The sensing device of claim 9, wherein the immunoassay test strip comprises multiple test pads, and wherein the at least one optical sensor further comprises:
    a separator between each of the test pads, wherein the separator comprises a polymer that swells when wet.

12. The sensing device of claim 9, wherein the at least one optical sensor further comprises:
    a layer of a superabsorbent polymer between the immunoassay test strip and the backing substrate.

13. The sensing device of claim 1, wherein the at least one optical sensor comprises: a microfluidic channel coated with a reagent-specific marker: an inlet at a first end of the microfluidic channel; an imaging device at a second end of the microfluidic channel opposite the inlet; a light source adjacent to the first end of the microfluidic channel; and a waveguide for directing light from the light source to the imaging device.

14. The sensing device of claim 13, wherein the imaging device comprises a camera on a chip.

15. The sensing device of claim 1, wherein a top of the float is recessed below a top surface of the sensor housing.

16. The sensing device of claim 1, wherein the strain gauge further comprises:
    a vent line leading from the bottom of the cavity out to an opposite side of the sensor housing from the cavity.

17. The sensing device of claim 1, wherein the float comprises at least one protrusion that compliments a track along a wall of the cavity which prevents any rotation of the float while permitting the float to move freely up and down within the cavity.

18. A sensing device, comprising: a housing; and sensors comprising two or more types of sensors hermetically sealed within the housing such that the sensing device and the sensors are fully submersible in a liquid analyte, wherein the housing comprises a flat top surface and a flat bottom surface opposite the flat top surface, wherein the flat top surface and the flat bottom surface are both circular such that the sensing device is shaped as a pellet having a diameter d of less than or equal to about 10 cm, and a thickness t of from about 1.25 mm to about 25 mm and ranges therebetween, wherein the sensing device once submerged in the liquid analyte is configured to collect data via the sensors and transmit the data, and wherein the sensors comprise at least one strain gauge comprising: a sensor housing having a cavity therein; a strain sensor on a bottom of the cavity; a float positioned within the cavity in contact with the strain sensor; and at least one optical sensor comprising: an immunoassay test strip.

19. A system for analysis of a liquid sample, the system comprising: at least one sensing device comprising a housing, and sensors comprising two or more types of sensors contained within the housing, wherein the housing hermetically seals the sensors such that the sensing device and the sensors are fully submersible in the liquid sample, and wherein the sensors comprise at least one strain gauge comprising: a sensor housing having a cavity therein; a strain sensor on a bottom of the cavity; a float positioned within the cavity in contact with the strain sensor; and at least one optical sensor comprising: an immunoassay test strip; and a data management system communicatively connected to the at least one sensing device, wherein the at least one sensing device once submerged in the liquid sample is configured to collect data via the sensors and transmit the data to the data management system.

20. The system of claim 19, wherein the two or more types of sensors comprise sensors selected from the group consisting of: electrical sensors, electrochemical sensors, optical sensors, pressure sensors, temperature sensors, specific gravity sensors, acoustic sensors, and combinations thereof.

21. The sensing device of claim 1, wherein the sensing device once submerged in the liquid analyte is configured to wirelessly transmit the data to a data management system.

22. The sensing device of claim 1, wherein the sensing device is configured to collect a unitized amount of a sample from the liquid analyte to a sensing surface comprising the sensors.

\* \* \* \* \*